United States Patent [19]

Kummer et al.

[11] 4,073,905
[45] Feb. 14, 1978

[54] 2-AMINO-4-PHENYL-2-IMIDAZOLINES AND SALTS THEREOF

[75] Inventors: Werner Kummer; Herbert Köppe; Helmut Stähle, all of Ingelheim am Rhein; Walter Haarmann, Biberach an der Riss, all of Germany

[73] Assignee: Boehringer Ingelheim GmbH, Ingelheim am Rhein, Germany

[21] Appl. No.: 775,736

[22] Filed: Mar. 9, 1977

Related U.S. Application Data

[63] Continuation-in-part of Ser. No. 379,750, July 16, 1973.

[30] Foreign Application Priority Data

July 19, 1972 Germany .............................. 2235314
July 19, 1971 Germany .............................. 2235328

[51] Int. Cl.² .................. C07D 403/12; C07D 413/12; A61K 31/495, A61K 31/535
[52] U.S. Cl. ............................... 424/248.56; 424/250; 260/268 PH; 260/268 H; 544/139; 548/351;
[58] Field of Search .............................. 544/132, 139; 260/268 H, 268 PH; 424/248.56, 250

[56] References Cited

U.S. PATENT DOCUMENTS 3,840,554   10/1974   Wittekind et al. ................... 544/139

OTHER PUBLICATIONS

Matier et al., 163rd ACS National Meeting, Boston, Mass., Abstracts of Papers, p. MEDI 2, (Mar. 1972).
Kummer et al., "Chem. Abstracts" vol. 80 (1974), No. 120,942g and No. 120,953m.

Primary Examiner—Natalie Trousof
Assistant Examiner—R. W. Ramsuer
Attorney, Agent, or Firm—Hammond & Littell

[57] ABSTRACT

Compounds of the formula

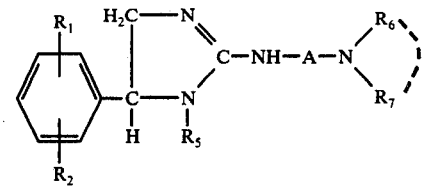

wherein
 $R_1$ and $R_2$, which may be identical to or different from each other, are each hydrogen, chlorine, bromine or alkyl of 1 to 3 carbon atoms,
 A is alkylene of 1 to 5 carbon atoms, and
 $R_6$ and $R_7$, together with each other and the nitrogen atom to which they are attached, form a heterocycle selected from the group consisting of morpholino, piperazino or N'-dimethylphenyl-piperazino, and
 $R_5$ is hydrogen, alkyl of 1 to 3 carbon atoms, hydroxyethyl, diethylamino-ethyl or furfuryl, provided, however, that $R_1$ and $R_2$ are other than both hydrogen or both alkyl at the same time, and non-toxic, pharmacologically acceptable acid addition salts thereof; the compounds as well as the salts are useful as hypotensives, platelet aggregation inhibitors and antiarrhythmics.

8 Claims, No Drawings

2-AMINO-4-PHENYL-2-IMIDAZOLINES AND SALTS THEREOF

This is a continuation-in-part of copending application Ser. No. 379,750 filed July 16, 1973.

This invention relates to novel 2-amino-4-phenyl-2-imidazolines and acid addition salts thereof, as well as to methods of preparing these compounds.

More particularly, the present invention relates to a novel class of 2-amino-4-phenyl-2-imidazolines of the formula

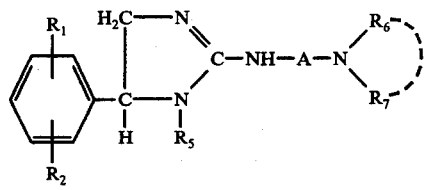

wherein $R_1$ and $R_2$, which may be identical to or different from each other, are each hydrogen, chlorine, bromine or alkyl of 1 to 3 carbon atoms, A is alkylene of 1 to 5 carbon atoms, and $R_6$ and $R_7$ together with each other and the nitrogen atom to which they are attached, form a heterocycle selected from the group consisting of morpholino, piperazino or N'-dimethylphenyl-piperazino, and $R_5$ is hydrogen, alkyl of 1 to 3 carbon atoms, hydroxyethyl, diethylamino-ethyl or furfuryl, provided, however, that $R_1$ and $R_2$ are other than both hydrogen or both alkyl at the same time, and non-toxic, pharmacologically acceptable acid addition salts thereof.

The compounds embraced by formula I are cyclic guanidines and may therefore exist in tautomeric forms; they comprise, furthermore, an asymmetric carbon atom, wherefore they may occur as racemates or optical antipodes.

The compounds of the present invention may be prepared by reacting an imidazoline of the formula

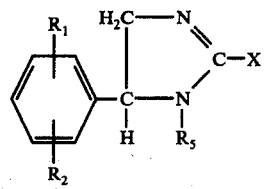

wherein $R_1$, $R_2$ and $R_5$ have the same meanings as in formula I and X is chlorine, bromine, iodine, lower alkoxy or lower alkyl-mercapto, with an amine of the formula

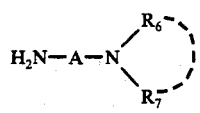

wherein A, $R_6$ and $R_7$ have the same meanings as in formula I.

The reaction is preferably performed in the absence of a solvent medium with the reactants in the molten state, but it will also proceed in the presence of an inert solvent, medium, such as an alkanol, a ketone or an ether.

The starting compounds are either known compounds or may be prepared by known methods.

For example, a compound of the formula II wherein X is halogen may be prepared by reacting a phenyl-substituted ethylenediamine of the formula

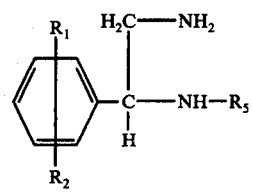

wherein $R_1$, $R_2$ and $R_5$ have the same meanings as in formula I, with a bifunctional carbonic acid derivative, such as phosgene, a chlorocarbonate or an orthocarbonate, to form a correspondingly substituted ethyleneurea, followed by halogenation with an inorganic acid halide, such as phosphorus oxychloride or oxybromide, phosphorus pentachloride or pentabromide, phosphorus trichloride, tribromide or triiodide, or a thionyl halide.

A compound of the formula II wherein X is alkyl-mercapto may be obtained, for example, by reacting a phenyl-substituted ethylenediamine of the formula IV with carbon disulfide to form a corresponding phenyl-substituted ethylenethiourea, and alkylation of the latter with an alkyl halide or an inorganic acid alkyl ester, such as dimethylsulfate.

A phenyl-substituted ethylenediamine of the formula IV may be prepared by reacting a correspondingly substituted benzaldehyde with ammonium cyanide to form an α-cyanobenzylamine, and hydrogenating the latter.

The compounds embraced by formula I are organic bases and therefore form acid addition salts with inorganic or organic acids. Examples of non-toxic, pharmacologically acceptable acid addition salts are those formed with hydrochloric acid, hydrobromic acid, hydrofluoric acid, hydroiodic acid, sulfuric acid, phosphoric acid, nitric acid, acetic acid, propionic acid, butyric acid, valeric acid, caproic acid, capric acid, oxalic acid, malonic acid, succinic acid, glutaric acid, maleic acid, fumaric acid, lactic acid, tartaric acid, citric acid, malic acid, gluconic acid, benzoic acid, p-hydroxy-benzoic acid, phthalic acid, cinnamic acid, salicyclic acid, ascorbic acid, 8-chloro-theophylline, methanesulfonic acid or the like.

The following examples illustrate the present invention and will enable others skilled in the art to understand it more completely. It should be understood, however, that the invention is not limited solely to the particular examples given below.

EXAMPLE 1

2-[(β-Morpholino-ethyl)-amino]-4-(2',6'-dichloro-phenyl)-2- imidazoline hydrochloride A mixture consisting of 6.0 gm (0.0202 mol) of 2-methylmercapto-4-(2',6'-dichloro-phenyl)-2-imidazoline hydrochloride and 3.25 gm (0.025 mol) of N-(β-amino-ethyl)-morpholine was melted by heating it for 30 minutes at 150° C. Thereafter, while still hot, the molten mass was dissolved in ethanol and reprecipitated from solution by addition of ether. The precipitate, which solidified after some time, was collected and recrystallized from ethanol/acetone and, for further purification, briefly heated in boiling water in the presence of activated charcoal. The mixture was filtered, the filtrate was evaporated to dryness, and the residue was washed with acetone, yielding 3.0 gm (41.8% of theory) of the white crystalline compound of the formula

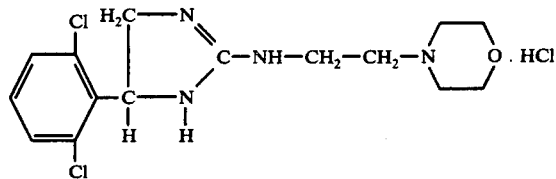

which had a melting point of 225° C.

EXAMPLE 2

Using a procedure analogous to that described in Example 1, 2-[(β-morpholino-ethyl)-amino]-4-(p-tolyl)-2-imidazoline oxalate, m.p. 132° C, was prepared from 2-methylmercapto-4-(p-tolyl)-2-imidazoline hydrochloride and N-(β-amino-ethyl)-morpholine.

EXAMPLE 3

Using a procedure analogous to that described in EXAMPLE 1, 2-[(γ-morpholino-n-propyl)-amino]-4-(2',6'-dichloro-phenyl)-2-imidazoline dioxalate, m.p. 185° C, was prepared from 2-methylmercapto-4-(2',6'-dichloro-phenyl)-2-imidazoline hydrochloride and N-(γ-amino-n-propyl)-morpholine.

EXAMPLE 4

Using a procedure analogous to that described in Example 1, 2-β-{N'-(2',6'-dimethyl-phenyl)-piperazino}-ethyl-amino]-4-(2',6'-dichloro-phenyl)-2-imidazoline dioxalate, m.p. 228° C, of the formula

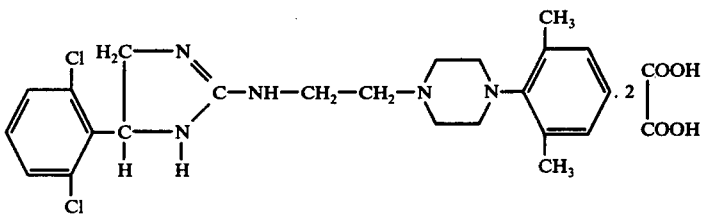

was prepared from 2-methylmercapto-4-(2',6'-dichloro-phenyl) -2-imidazoline hydrochloride and [β-{N'-(2,6-dimethyl-phenyl) -piperazino}-ethyl]-amino.

EXAMPLE 5

Using a procedure analogous to that described in Example 1, 2-[(β-piperazino-ethyl)-amino]-3-methyl-4-(2',6'-dichloro-phenyl)-2-imidazoline trioxalate, m.p. 162° C., was prepared from 2-methylmercapto-3-methyl-4-(2',6'-dichlorophenyl)-2-imidazoline hydrochloride and (β-piperazino-ethyl)-amine.

The compounds of the present invention, that is, those embraced by formula I and their non-toxic, pharmacologically acceptable acid addition salts, have useful pharmacodynamic properties. More particularly, they exhibit hypotensive, platelet aggregation inhibiting and antiarrhythmic activities in warm-blooded animals, such as rats, cats, and dogs.

For pharmaceutical purposes the compounds according to the present invention are administered to warm-blooded animals perorally or parenterally as active ingredients in customary dosage unit compositions, that is, compositions in dosage unit form consisting essentially of an inert pharmaceutical carrier and one effective dosage unit of the active ingredient, such as tablets, coated pills, capsules, wafers, powders, solutions, suspensions, emulsions, syrups, suppositories and the like. One effective dosage unit of the compounds according to the present invention is from 0.0008 to 1.34 mgm/kg body weight, preferably 0.0016 to 0.34 mgm/kg body weight.

The following examples illustrate a few pharmaceutical dosage unit compositions comprising a compound of the present invention as an active ingredient and represent the best modes contemplated of putting the invention into practical use. The parts are parts by weight unless otherwise specified.

EXAMPLE 6

Tablets

The tablet composition is compounded from the following ingredients:

| | |
|---|---|
| 2-[(β-Morpholino-ethyl)-amino]-4-(2',6'-dichloro-phenyl)-2-imidazoline hydrochloride | 1 parts |
| Lactose | 65 parts |
| Corn starch | 125 parts |
| Sec. calcium phosphate | 40 parts |
| Soluble starch | 3 parts |
| Magnesium stearate | 2 parts |
| Colloidal silicic acid | 4 parts |
| Total | 240 parts |

Preparation

The imidazoline compound is intimately admixed with a substantial portion of each of the other ingredients except the soluble starch, the resulting mixture is moistened with an aqueous solution of the soluble starch, the moist mass is granulated through a screen, the granulate is dried and then admixed with the remainder of the inert ingredients, and the composition is compressed into 240 mgm-tablets in a conventional tablet making machine. Each tablet contains 1 mgm of the imidazoline compound and is an oral dosage unit composition with effective hypotensive action. EXAMPLE 7

Hypodermic Solution

The solution is compounded from the following ingredients:

| | |
|---|---|
| 2-[(β-Morpholino-ethyl-amino]-4-(2',6'-dichloro-phenyl)-2-imidazoline hydrochloride | 1 parts |
| Sodium chloride | 18 parts |
| Distilled water    q.s.ad | 2000 parts |

Preparation

The imidazoline compound and the sodium chloride are dissolved in the distilled water, the solution is filtered until free from suspended particles, and the filtrate is filled into 2 cc - ampules in a atmosphere of nitrogen and under aseptic conditions. Each ampule contains 1 mgm of the imidazoline compound, and the contents are in injectable dosage unit composition with effective hypotensive action.

EXAMPLE 8

Drop Solution

The solution is compounded from the following ingredients:

| | |
|---|---:|
| 2-[(β-Piperazino-ethyl)-amino]-3-methyl-4-(2',6'-dichloro-phenyl)-2-imidazoline hydrochloride | 20 parts |
| Methyl p-hydroxy-benzoate | 7 parts |
| Propyl p-hydroxy-benzoate | 3 parts |
| Demineralized water    q.s.ad | 100,000 parts by vol. |

Preparation

The ingredients are dissolved in a sufficient amount of the demineralized water, the solution is diluted to the indicated volume with additional demineralized water, the aqueous solution is filtered, and the filtrate is filled into 100 ml - bottles. 5 ml (about 20 drops) of the solution contain 1 mgm of the imidazoline compound and are an oral dosage unit composition with effective hypotensive action.

Analogous results are obtained when any one of the other imidazoline derivatives embraced by formula I or a non-toxic, acid addition salt thereof is substituted for the particular imidazoline in Examples 6 through 8. Likewise, the amount of active ingredient in these illustrative examples may be varied to achieve the dosage unit range set forth above, and the amounts and nature of the inert pharmaceutical carrier ingredients may be varied to meet particular requirements.

While the present invention has been illustrated with the aid of certain specific embodiments thereof, it will be readily apparent to others skilled in the art that the invention is not limited to these particular embodiments, and that various changes and modifications may be made without departing from the spirit of the invention or the scope of the appended claims.

We claim:
1. A compound of the formula

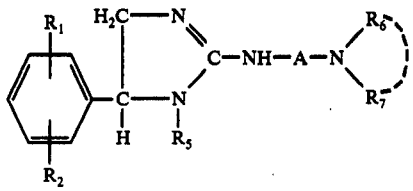

wherein
$R_1$ and $R_2$, which may be identical to or different from each other, are each hydrogen, chlorine, bromine or alkyl of 1 to 3 carbon atoms, A is alkylene of 1 to 5 carbon atoms, and $R_6$ and $R_7$, together with each other and the nitrogen atom to which they are attached, form a heterocycle selected from the group consisting of morpholino, piperazino or N'-dimethylphenyl-piperazino, and $R_5$ is hydrogen, alkyl of 1 to 3 carbon atoms, hydroxyethyl, diethylamino-ethyl or furfuryl, provided, however, that $R_1$ and $R_2$ are other than both hydrogen or both alkyl at the same time, or a non-toxic, pharmacologically acceptable acid addition salt thereof.

2. A compound of claim 1 which is 2-[(β-morpholino-ethyl)-amino]-4-(2',6'-dichloro-phenyl)-2-imidazoline or a non-toxic, pharmacologically acceptable acid addition salt thereof.

3. A compound of claim 1, which is 2-[(β-morpholino-ethyl)-amino]-4-(p-tolyl)-2-imidazoline or a non-toxic, pharmacologically acceptable acid addition salt thereof.

4. A compound of claim 1, which is 2-[(γ-morpholino-n-propyl)-amino]-4-(2',6'-dichloro-phenyl)-2-imidazoline or a non-toxic, pharmacologically acceptable acid addition salt thereof.

5. A compound of claim 1, which is 2-[(β-piperazino-ethyl)-amino]-3-methyl-4-(2',6'-dichloro-phenyl)-2-imidazoline or a non-toxic, pharmacologically acceptable acid addition salt thereof.

6. A compound of claim 1, which is 2-[β-{N'-(2',6'-dimethyl-phenyl)-piperazino}-ethylamino]-4-(2',6'-dichlorophenyl)-2-imidazoline or a non-toxic, pharmacologically acceptable acid addition salt thereof.

7. A pharmaceutical dosage unit composition consisting of an inert pharmaceutical carrier and an effective hypotensive amount of a compound of claim 1.

8. The method of lowering the blood pressure of a warm-blooded animal in need of such treatment, which comprises administering to said animal an effective hypotensive amount of a compound of claim 1.

* * * * *